(12) United States Patent
Hartlaub et al.

(10) Patent No.: US 6,198,972 B1
(45) Date of Patent: Mar. 6, 2001

(54) CONTROL OF EXTERNALLY INDUCED CURRENT IN IMPLANTABLE MEDICAL DEVICES

(75) Inventors: Jerome T. Hartlaub, St. Paul, MN (US); Marc T. Stein, Chandler, AZ (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 08/847,642

(22) Filed: Apr. 30, 1997

(51) Int. Cl.[7] ........................................ A61N 1/08
(52) U.S. Cl. ................................................ 607/63
(58) Field of Search ................... 607/2, 63, 64

(56) References Cited

U.S. PATENT DOCUMENTS

| | | | |
|---|---|---|---|
| 4,745,923 | * 5/1988 | Winstrom | 607/63 |
| 5,584,870 | * 12/1996 | Single et al. | 607/63 |
| 5,591,218 | * 1/1997 | Jacobson | 607/63 |
| 5,649,965 | * 7/1997 | Pons et al. | 607/63 |

* cited by examiner

Primary Examiner—Scott M. Getzow
(74) Attorney, Agent, or Firm—Banner & Witcoff, Ltd.

(57) ABSTRACT

A current limiting apparatus that is adapted to be operatively connected as part of a conductive loop formed by a medical device implanted within a living organism having electrically excitable tissue. This apparatus limits unwanted current in the conductive loop that may be induced by a significant level of an external signal such as a time-alternating electromagnetic field. This apparatus includes a switch for introducing a high impedance into the conductive loop when the switch is turned off. The apparatus also includes a control circuit that controls the switch to be turned on when the conductive loop should be closed to stimulate the electrically excitable tissue for a therapeutic effect. The control circuit turns the switch off whenever the living organism enters an area having a significant level of external signal that may induce unwanted current in the conductive loop to limit the unwanted current. The living organism can manually initiate turning off the switch when the living organism is about to enter an area having such an external signal. Alternatively, such an external signal is sensed to turn the switch off automatically when such an external signal is sensed.

8 Claims, 5 Drawing Sheets

CONTROL OF EXTERNALLY INDUCED CURRENT IN IMPLANTABLE MEDICAL DEVICES

BACKGROUND OF THE INVENTION

1. Field of the Invention

This invention relates generally to implantable medical devices, and more particularly to a method and apparatus for limiting unwanted current flow through electrically excitable tissue resulting from application of an external signal on an implanted medical device.

2. Description of the Related Art

The use of implantable medical devices for electrical stimulation of electrically excitable tissue is well known in the medical arts. Electrical stimulation of brain tissue has been used for tremor suppression. Moreover, electrical stimulation of peripheral nerve tissue has been used to promote blood circulation in patients having peripheral vascular disease. Additionally, electrical stimulation of the brain and nerve tissue of the spinal cord has been used for pain management. In such devices, electrodes deliver the stimulation signal to the electrically excitable tissue. The electrodes are operatively connected to an implantable pulse generator which is packaged in a case that is adapted to be implantable. Those electrodes are coupled to that pulse generator by a conductive lead wire.

A user having such an implanted medical device during normal life activities may be forced to go through a time-alternating electromagnetic field. Prevalent examples of sources of electromagnetic field are Electronic Article Surveillance (EAS) systems. Such systems detect theft and are found in the exit doorways of many stores and libraries. EAS systems typically emit an AC electromagnetic field for detecting theft of articles that have an attached electromagnetic tag.

When the user having an implanted medical device walks through an EAS system that emits a significant level of AC electromagnetic field, current may be induced in the electrically excitable tissue by the Faraday effect. According to the Faraday effect, when a conductive loop is disposed within a time-alternating electromagnetic field, a current is induced in that conductive loop. With the implanted medical device within the user, the conductive loop consists of the stimulation electrodes, the lead wire, the implantable pulse generator having a case, and the conductive medium of the body including the electrically excitable tissue between the stimulation electrodes and the case. The case in some implantable medical devices acts as a reference return electrode with respect to the stimulation electrodes and is composed of electrically conductive material.

The user may experience unwanted physiological effects from the current that is induced in the electrically excitable tissue of that conductive loop. This current may cause uncontrolled excitation of electrically excitable tissue which can lead to pain sensations and unwanted motor responses for the user. Thus, means for controlling that induced current is desired.

Objects of the Invention

Accordingly, a primary object of the present invention is to limit the current that may be induced within the conductive loop formed by an implanted medical device when a significant level of external signal such as an electromagnetic field is present. The induced current is limited automatically upon sensing a significant level of an external signal or manually with the user controlling the opening of the conductive loop when the user is about to enter an area having a significant level of external signal.

SUMMARY OF THE INVENTION

In a principal aspect, the present invention takes the form of an apparatus and method for limiting current flow, induced when the level of an external signal is greater than an external signal threshold level, in a conductive loop formed by a medical device implanted within a living organism having electrically excitable tissue. The present invention includes a switch that is adapted to be operatively connected within the conductive loop which includes the implanted medical device and the electrically excitable tissue. Additionally, a control circuit controls the switch to turn the switch on when the medical device is stimulating the electrically excitable tissue to achieve a therapeutic effect if the level of the external signal is less than the external signal threshold level. Moreover, the control circuit controls the switch to turn off whenever the level of the external signal is greater than the external signal threshold level, to thereby introduce a high impedance into the conductive loop.

The present invention can be applied to particular advantage when used with a sensor for sensing when the level of the external signal is greater than the external signal threshold level. The control circuit would automatically turn the switch off when the sensor senses that the level of the external signal is greater than the external signal threshold level. Alternatively, the living organism, having the implanted medical device, manually initiates the opening of the conductive loop. In this manner, the conductive loop can be opened manually to limit unwanted current that can result from application of a significant level of external signal on a closed conductive loop.

These and other features and advantages of the present invention will be better understood by considering the following detailed description of the invention which is presented with the attached drawings.

DESCRIPTION OF THE PREFERRED EMBODIMENTS

Figure 1A:
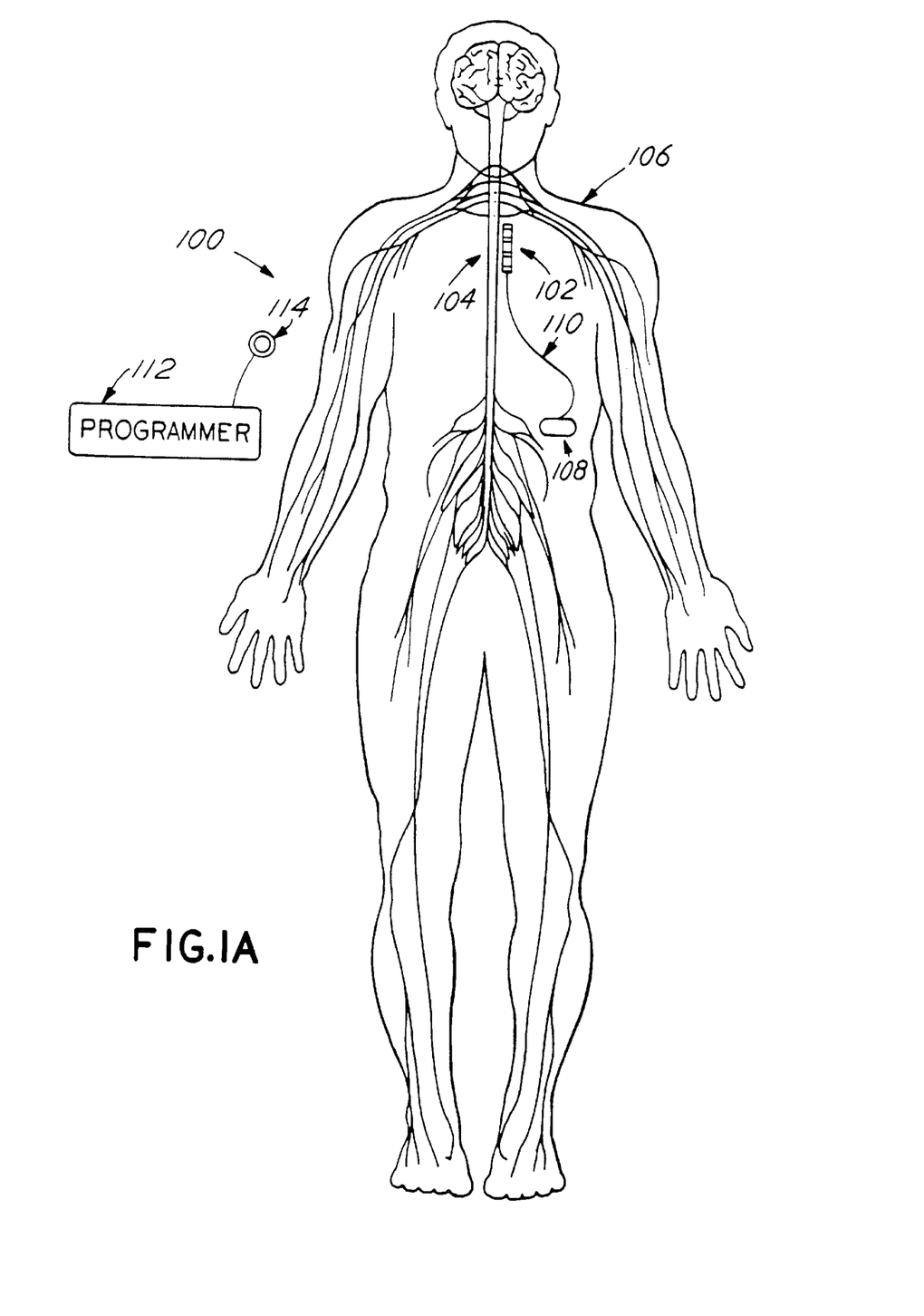
FIG. 1A shows an electrical stimulation system which forms a closed conductive loop when implanted within a human body.

Referring to FIG. 1A, an electrical stimulation system 100 comprises stimulation electrodes 102 implanted near electrically excitable tissue 104 of a human body 106 of a user. The electrically excitable tissue in FIG. 1A is nerve tissue within the spinal column. However, electrodes of implanted medical devices are also commonly implanted near other types of nerve tissue such as peripheral nerve tissue and brain tissue. The electrical stimulation system 100 also includes an implantable pulse generator 108 which provides the stimulation signals to be applied on the stimulation electrodes 102 via a conductive lead wire 110.

A programmer 112 sends messages to the implantable pulse generator 108 to modify the stimulation signals to be applied on the electrodes 102. The programmer controls the pulse generator by radio frequency communication to the pulse generator via an antenna 114 and corresponding receiver in the generator 108. An example of such an electrical stimulation system is the ITREL II system available from Medtronic, Inc., Minneapolis, Minn. While the preferred system employs fully implanted elements, systems employing partially implanted generators and radio-frequency coupling may also be used in the practice of the present invention. Such systems are also available from Medtronic, Inc. under the trademarks X-trel and Mattrix.

The electrical stimulation system 100 of FIG. 1A is implanted to cause a therapeutic effect of pain reduction by inducing an action potential in the electrically excitable tissue 104. The implantable pulse generator generates the stimulation signals to be applied on the electrodes 102. For example, the induced action potential in the nerve fibers of the spinal cord can reduce pain experienced by the human body 106.

The preferred embodiment of the present invention is described for the electrical stimulation system 100 used to achieve the therapeutic effect of pain reduction in the human body 106. However, it should be appreciated that the present invention can be used with other implantable medical devices for achieving other therapeutic effects aside from just pain management. Additionally, it should be appreciated that the present invention can be used for medical devices implanted in other living organisms aside from just a human body.

In the implanted medical device of FIG. 1A, a conductive loop is formed by the stimulation electrodes 102, the lead wire 110, the implantable pulse generator 108 having a conductive case, and a conductive medium of the human body 106 between the stimulation electrodes and the conductive case of the implantable pulse generator. The case of the implantable pulse generator can act as a reference electrode with respect to the stimulation electrodes. The conductive medium of the human body includes the electrically excitable tissue 104.

When the user having such an implanted medical device enters an area having a significant level of time-alternating electromagnetic field, a current may be induced in the conductive loop formed by the implanted medical device and by the electrically excitable tissue in accordance with the Faraday effect. According to the Faraday effect, when a time-alternating electromagnetic field is applied on a conductive loop, a current is induced in that conductive loop. Common sources of time-alternating electromagnetic field are Electronic Article Surveillance (EAS) systems installed on exit doorways of many stores and libraries. Other sources of time-alternating electromagnetic fields include Nuclear Magnetic Resonance Imaging (NMRI) systems, security screening corridors found in airports, and cellular telephones.

When such an external signal induces a current in the conductive loop and in turn the electrically excitable tissue, the user may experience pain and uncontrollable motor responses. Thus, this induced current is unwanted, and the present invention limits this unwanted current.

In the implanted medical device system 100 of FIG. 1A, the implantable pulse generator 108 generates stimulation signals to be applied on the stimulation electrodes 102. The conductive loop formed by the implanted medical device and by the electrically excitable tissue is closed when stimulation signals are applied on the stimulation electrodes to induce an action potential in the electrically excitable tissue 104. That action potential creates a current in the electrically excitable tissue to cause a therapeutic effect. In that case, the conductive loop is closed such that current can flow in the conductive loop.

When the user enters an area with a significant level of external signal such as a time-alternating electromagnetic field, that external signal may induce unwanted current in that conductive loop. In that case, the conductive loop is opened to limit the induced unwanted current. The general embodiment of the present invention opens that conductive loop by introducing a switch into that conductive loop.

Figure 1B:
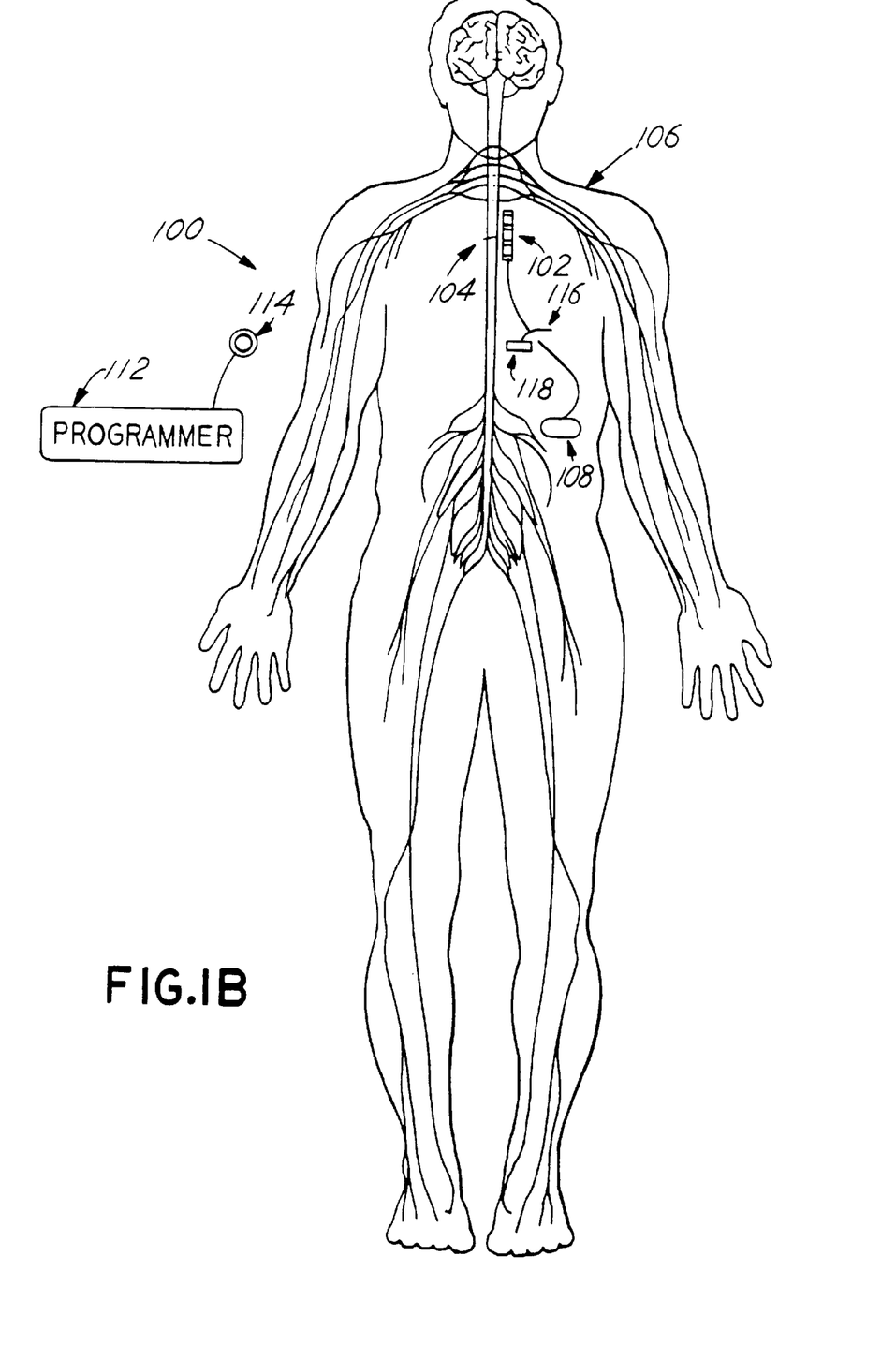
FIG. 1B shows the electrical stimulation system of FIG. 1A with the further inclusion of a switch for opening the conductive loop formed by the implanted electrical stimulation system, according to a preferred embodiment of the present invention.

Referring to FIG. 1B, the electrical stimulation system 100 of FIG. 1A is shown with similar elements having the same number label. The electrical stimulation system 100 of FIG. 1B further includes a switch 116 operatively connected between the case of the pulse generator 108 and the stimulation electrodes 102. However, the switch 116 can be inserted within any part of the conductive loop formed by the implanted medical device for proper operation of the present invention. In the preferred embodiment of the present invention, the switch 116 and a sensor circuit 118 used with that switch are disposed inside the implantable pulse generator 108.

The switch 116 is opened to prevent flow of unwanted current induced in the conductive loop by an external signal. The switch can be opened automatically upon sensing a significant level of external signal. The sensor circuit 118 is operatively connected to the switch 116 to open that switch when the sensor circuit senses a significant level of the external signal.

The sensor circuit 118 can sense the level of the external signal directly, and in that case, the sensor circuit can be located anywhere on or near the human body 106. In an alternative embodiment, the sensor can detect the level of unwanted current within the conductive loop formed by the medical device. A significant level of this unwanted current is an indirect indication of the presence of a significant level of external signal. Alternatively, the switch 116 can be a electromagnetically sensitive switch that opens when the level of the external signal is greater than an external signal threshold level, and in that case, the sensor circuit 118 is not required.

The switch closes when the level of the external signal is less than the external signal threshold level. External signals such as radio frequency signals are prevalent in the surroundings of a user. However, when the level of external signal exceeds the external signal threshold level, that external signal may induce enough unwanted current in the closed loop to cause undesirable physiological effects.

In an alternative embodiment, the user having the implanted medical device can actively open the switch 116. For example, if the switch were magnetically sensitive, then when the user is about to enter an area where the level of the external signal is greater than the external signal threshold level, the user brings a magnet near the switch 116 in order to manually open the switch 116. When the user perceives that a significant level of external signal is no longer present, the user again brings the magnet near the switch 116 to close the switch 116. In that embodiment also, the sensor circuit 118 is not required.

Figure 2:
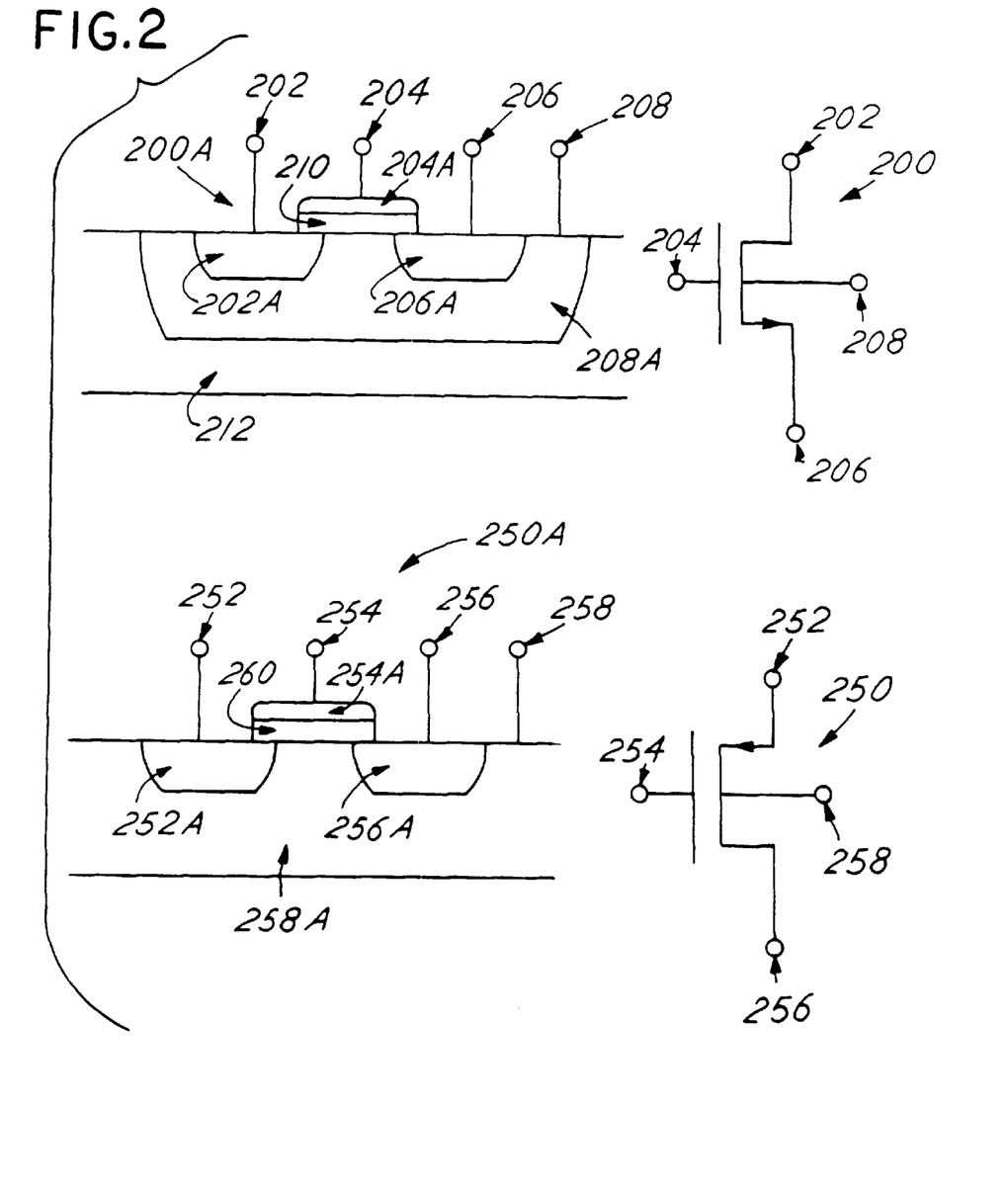
FIG. 2 shows simple switch devices and the cross sections of those switch devices fabricated with semiconductor integrated circuit technology.

Referring to FIG. 2, two common means for implementing the switch 116 in CMOS IC technology are the NMOS- FET 200 and the PMOSFET 250. The NMOSFET (N-Channel Metal Oxide Semiconductor Field Effect Transistor) has a cross section 200A, and the PMOSFET (P-Channel Metal Oxide Semiconductor Field Effect Transistor) 250 has a cross section 250A.

The cross section 200A of the NMOSFET shows a N-type doped drain region 202A that forms a first drain terminal 202, a conductive gate region 204A that forms a first gate terminal 204, and a N-type doped source region 206A that forms a first source terminal 206. The conductive gate region 204A sits on top of a silicon dioxide layer 210. Also, a P-well region 208A that forms a P-well terminal 208 is also shown. The P-well is a P-type doped region and sits within a N-type substrate region 212.

Similarly, the cross section 250A of the PMOSFET shows a P-type doped source region 252A that forms a second source terminal 252, a conductive gate region 254A that forms a second gate terminal 254, and a P-type doped drain region 256A that forms a second drain terminal 256. The conductive gate region 254A sits on top of a silicon dioxide layer 260. Those P-type doped drain and source regions sit within a N-type doped substrate region 258A that forms a N-substrate terminal 258. With the use of such devices, the switch 116 and the sensor circuit 118 for controlling the switch are located within the implantable pulse generator 108.

Either the NMOSFET or the PMOSFET can be inserted as the switch 116 of FIG. 1B. The gate terminal of such a switch device is controlled to close the conductive loop when the electrically excitable tissue is stimulated for therapeutic effect. Also the gate terminal of such a switch device is controlled to open the conductive loop when the user is about to enter an area having a significant level of external signal.

However, if only a switch device such as one of the NMOSFET or the PMOSFET were inserted in the conductive loop, current may still be induced in the conductive loop even when the switch device is turned off. Parasitic current can still flow in such a switch device even when the switch device is turned off. Referring to FIGS. 1B and 2, when a significant level of an external signal such as a time alternating electromagnetic field is applied on the medical device 100 implanted within the body 106, current may be induced in the conductive loop formed by the implanted medical device.

When the switch is opened to limit current flow, a charge build-up can cause a voltage change at points in the conductive loop. For example, the case holding the implantable pulse generator 108 has been shown to have a voltage build-up as high as ±8 Volts when a significant level of external signal is present. Assume that the drain terminal of a NMOSFET were operatively connected to that case and that −8 V were to build up on that case. Then, referring to the cross section 200A of the NMOSFET, an unwanted parasitic current may flow from a forward-biased P-N junction formed by the P-well region 208A and the N-type doped drain region 202A that is operatively connected to the case. Similarly, assume that the drain terminal of a PMOSFET were operatively connected to that case and that +8 V were to build up on that case. Then, referring to the cross section 250A of the PMOSFET, an unwanted parasitic current may flow from a forward-biased P-N junction formed by the N-type substrate region 258A and the P-type doped drain 252A that is operatively connected to the case.

Figure 3:
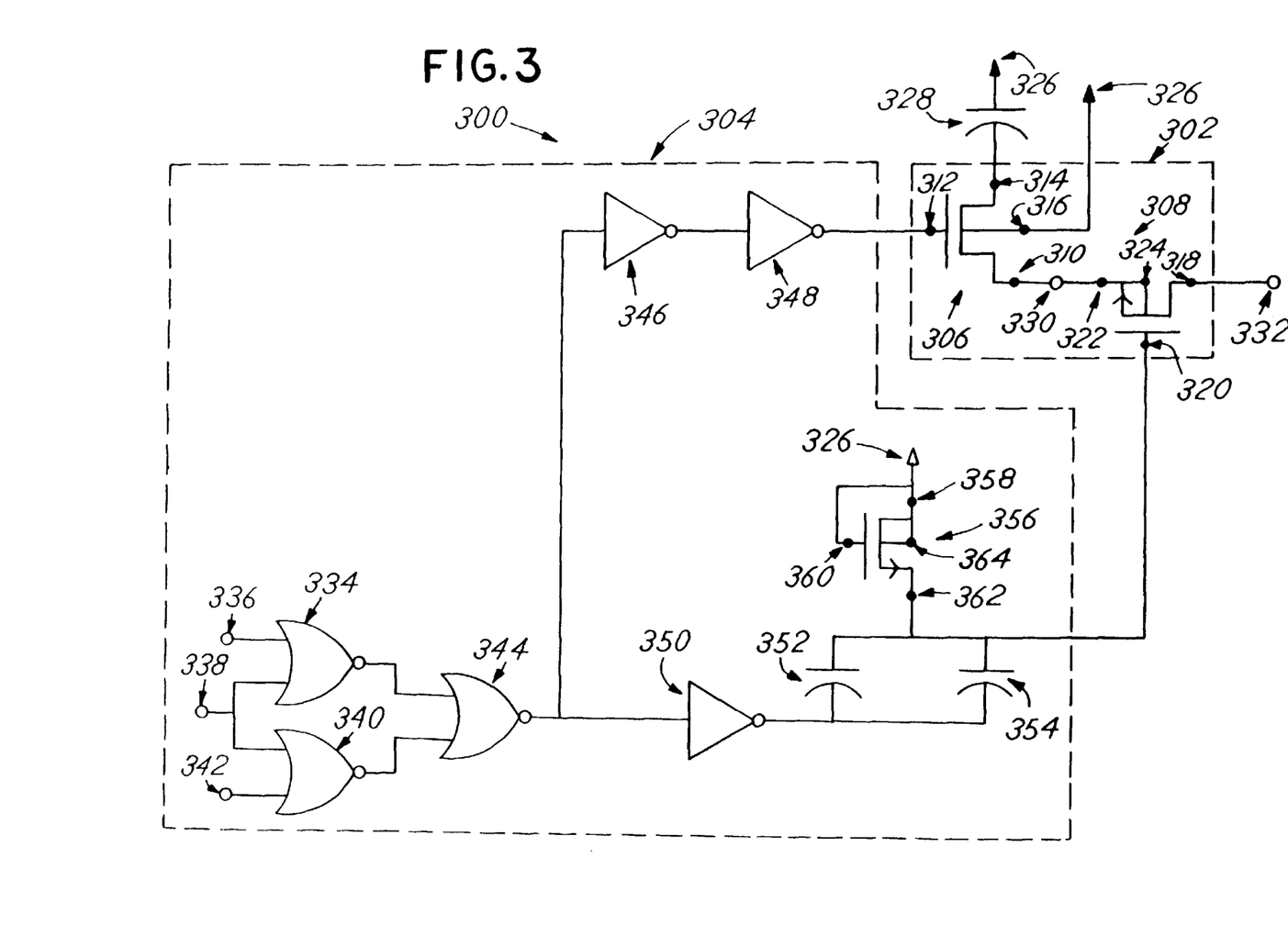
FIG. 3 shows a current limiting circuit according to a preferred embodiment of the present invention.

Thus, simply a NMOSFET or a PMOSFET may not sufficiently limit the unwanted current that may be induced by an external signal. FIG. 3 shows a current limiting circuit 300 that can limit unwanted current even when there is a voltage build-up at a node within the conductive loop. The current limiting circuit 300 of FIG. 3 comprises a switch 302 shown within dashed lines and a control circuit 304 shown within dashed lines.

The switch 302 includes a PMOSFET 306 as a first switch device and a NMOSFET 308 as a second switch device. The PMOSFET has a first drain terminal 310, a first gate terminal 312, a first source terminal 314, and a N-type substrate terminal 316. The NMOSFET has a second drain terminal 318, a second gate terminal 320, a second source terminal 322, and a P-well terminal 324. The PMOSFET and the NMOSFET have the same cross section as those shown in FIG. 2. The first source terminal 314 of the PMOSFET is operatively connected to a positive power supply 326 via a first coupling capacitor 328. The N-substrate terminal 316 of the PMOSFET is also operatively connected to the positive power supply. The first drain terminal 310 of the PMOSFET is operatively connected to the second source terminal 322 of the NMOSFET at a node 330.

The second drain terminal 318 of the NMOSFET is operatively connected to the output node 332 of the current limiting circuit 300. This output node is operatively connected to the implanted medical device. For example, in the implanted electrical stimulation system of FIG. 1B, the current limiting circuit 300 is part of the implantable pulse generator, and the output node 332 is operatively connected to the case of the implantable pulse generator 108. The P-well terminal 324 of the NMOSFET 308 is operatively connected to the second source terminal 322.

The control circuit 304 is operatively connected to the first gate terminal 312 of the PMOSFET 306 and to the second gate terminal 320 of the NMOSFET 308 to bias those switch devices to be on or off. The control circuit includes a first NOR gate 334 having a first control terminal 336 as an input and a second control terminal 338 as an input. The control circuit also includes a second NOR gate 340 having the second control terminal 338 as an input and a third control terminal 342 as an input. The output of the first NOR gate 334 and the output of the second NOR gate 340 are inputs to a third NOR gate 344.

The output of the third NOR gate 344 is operatively connected to the first gate terminal 312 of the PMOSFET 306 through a first inverter 346 and a second inverter 348. The output of the third NOR gate 344 is also operatively connected to the second gate terminal 320 of the NMOSFET 308 through a third inverter 350 and through a pair of a second coupling capacitor 352 and a third coupling capacitor 354 which are connected in parallel.

The control circuit also includes a biasing NMOSFET 356 having a third drain terminal 358, a third gate terminal 360, a third source terminal 362, and a third P-well terminal 364. The drain terminal of that transistor is diode connected to its gate terminal, and both its drain and gate terminals are connected to the positive power supply 326. In addition, the P-well terminal 364 of that transistor is operatively connected to the positive power supply to form another forward biased diode connected between the P-well and the N-type doped source of NMOSFET 356. That source terminal is operatively connected to the second gate terminal 320 of NMOSFET 308.

The operation of the current limiting circuit 300 of FIG. 3 is now described. Referring to the implanted medical device 100 of FIG. 1B, the output node 332 of the current limiting circuit 300 is operatively connected to the case of the implantable pulse generator 108. The positive power supply 326 is also part of the implantable pulse generator which is operatively coupled to the stimulation electrodes 102. Thus, the switch 302 is connected as part of the conductive loop formed by the implanted electrical stimulation system 100. The switch is then connected in series between the stimulation electrodes and the case of the implantable pulse generator 108 in that conductive loop.

The current limiting circuit operates to close the conductive loop by turning on both the PMOSFET 306 and the NMOSFET 308 of the switch 302 when the implanted medical device stimulates the electrically excitable tissue to achieve a therapeutic effect. The conductive loop is opened by introducing a high impedance at the output node 332 when the level of external signal such as a time-alternating electromagnetic field is greater than an external signal threshold level. This high impedance is generated by maintaining both of the PMOSFET 306 and the NMOSFET 308 off whenever the level of an external signal is greater than the external signal threshold level.

The first control terminal 336 receives a first control signal, and the third control terminal 342 receives a second control signal. The second control terminal 338 receives an over-sense control signal. The first control signal goes low when stimulation signals are applied on the electrically excitable tissue to source current into the tissue. The second control signal goes low when stimulation signals are applied on the electrically excitable tissue to sink current out of the tissue. This electrical stimulation of the tissue by the implanted medical device causes beneficial therapeutic effects. Accordingly, the conductive loop formed by the implanted medical device is closed during this stimulation process.

Referring to FIG. 3, for now assume that the over-sense control signal applied on the second control terminal 338 is tied low. Then, when either one of the first control signal applied on the first control terminal 336 or the second control signal applied on the second control terminal 342 goes low, the output of the third NOR gate 344 goes low. In turn, the first gate terminal 312 of the PMOSFET 306 goes low, and the second gate terminal 320 of the NMOSFET 308 goes high. The diode formed by the diode connection of the biasing NMOSFET 356 turns off. A low voltage on the gate terminal of the PMOSFET 306 turns on that PMOSFET.

A high voltage on the gate terminal of the NMOSFET 308 turns on that NMOSFET. When the output of the third NOR gate 344 was high, the diode formed by the biasing NMOSFET 356 was turned on, and the voltage at the gate terminal of the NMOSFET 308 was at the positive power supply voltage $V_{DD}$ minus the diode drop of the NMOSFET 356 $V_{th}$, ($V_{DD}-V_{th}$). Then when the output of the third NOR gate 344 goes low, the voltage at the output of the inverter 350 goes high, the diode formed by NMOSFET 356 turns off, and the voltage on the gate terminal of NMOSFET 308 rises from $V_{DD}-V_{th}$ to $V_{DD}-V_{th}+V_{DD}=2V_{DD}-V_{th}$. This high voltage on the gate terminal of NMOSFET 308 ensures that this NMOSFET remains on in the case either one of the first control signal applied on the first control terminal 336 or the second control signal applied on the second control terminal 342 goes low.

In this manner, both the PMOSFET and the NMOSFET within the switch 302 are on. In that case, the conductive loop is closed such that current flows within that loop to achieve a therapeutic effect.

The conductive loop formed by the implanted medical device is opened with a high impedance introduced into the conductive loop when the electrically excitable tissue is not being stimulated for therapeutic effect. In that condition, both the first control signal and the second control signal are set high. With those control signals, the output of the third NOR gate 344 goes high.

In turn, the first gate terminal 312 of the PMOSFET 306 goes high. The diode formed by the diode connection of the biasing NMOSFET 356 turns on. Thus, the second gate terminal 320 of the NMOSFET 308 is at a diode voltage drop, $V_{th}$, from the voltage of the positive power supply, $V_{DD}$. A high voltage on the gate terminal of the PMOSFET 306 turns that PMOSFET off. A voltage of a gate to source voltage drop $V_{th}$ of the diode-connected transistor 356 from the voltage on the positive power supply, $V_{DD}$, applied on the gate terminal of the NMOSFET 308 keeps that NMOSFET off.

In addition, the current limiting circuit 300 of FIG. 3 maintains a high impedance in the conductive loop formed by the implanted medical device even when there is a voltage build-up at one of the nodes in the conductive loop. In the current limiting circuit 300, the output node 332 of the switch 302 is tied to the conductive case of the implantable pulse generator 108 of FIG. 1B. When an external signal such as a time-alternating magnetic field is present, induced current in the conductive loop can cause a voltage build-up on the conductive case of the implantable pulse generator. This voltage build-up can result in voltages as high as ±8 V at the case. In contrast to the simple switch devices of FIG. 2, the current limiting circuit 300 can maintain the high impedance within the conductive loop even with such a voltage build-up.

For example, with the output node 332 tied to the case of the pulse generator 108, assume that the voltage on that case and in turn on the output node has built up to −8 V. Referring to FIGS. 2 and 3, with such a high negative voltage on the output node, the NMOSFET 308 may have a forward biased PN junction between the P-well region and the N-type doped drain of that NMOSFET. Thus, unwanted current flows in that parasitic path. In addition, since MOSFET devices in CMOS technology are symmetrical, the N-type doped region of NMOSFET 308 tied to the output node can act as a source. With −8 V applied on that terminal, NMOSFET 308 may turn on.

However, note that the PMOSFET 306 of the switching circuit is kept off with its source to gate voltage $V_{SG}$ still being sufficiently low. This PMOSFET is in the path of the parasitic PN junction of the NMOSFET 308 and in the path of the drain to source terminals of that NMOSFET. Thus, the PMOSFET blocks the unwanted parasitic current caused by the high negative voltage build-up on the case of the implantable pulse generator 108.

Similarly, assume that the voltage on the output node 332 has built up to a high positive voltage such as +8 V. Referring to FIGS. 2 and 3, with such a high positive voltage, the PMOSFET 306 has a parasitic forward biased PN junction between the P-type doped drain region and the N-substrate region. Thus, unwanted current flows in that parasitic path.

However, note that NMOSFET 308 is in the path of that parasitic PN junction. The NMOSFET blocks the parasitic current in that PN junction. Note that the N-substrate 316 of the PMOSFET is tied to the positive power supply. Thus, for the parasitic PN junction to conduct that unwanted current, the drain terminal 310 of the PMOSFET must be set at a voltage higher than the voltage of the positive power supply $V_{DD}$ by a threshold voltage of that PN junction, $V_{th}$.

That drain terminal 310 of the PMOSFET 306 is operatively connected to the source terminal 322 of the NMOSFET 308. The gate terminal 320 of the NMOSFET is set at a diode voltage drop which is typically equal to a threshold voltage of that diode junction, $V_{th}$, from the positive power supply. If the drain terminal 310 of the PMOSFET (which is also the source terminal 322 of the NMOSFET) were to go above $V_{DD}+V_{th}$ such that the parasite PN junction of the PMOSFET turns on, then the gate to source voltage $V_{GS}$ of the NMOSFET becomes too low for the NMOSFET to turn on. In that case, the NMOSFET turns off, and the NMOSFET which is in the path of the parasitic PN junction of the PMOSFET blocks the unwanted current flow through that parasitic PN junction. Thus, unwanted current, caused by the high positive voltage build-up on the case of the implantable pulse generator 108, is prevented.

In this manner, the current limiting circuit 300 blocks any unwanted current flow that may be induced in the conductive loop formed by the implanted medical device. Thus, when this circuit is inserted in that conductive loop, the switch 302 is kept off to introduce and maintain a high impedance within that conductive loop.

Thus far, the over-sense control signal on the second control terminal 338 has been tied low. In that state, only the first and second control signals dictate whether the switch 302 is on or off. Those control signals close the conductive loop when stimulation signals are applied on the electrically excitable tissue for a therapeutic effect and open the conductive loop otherwise. However, with those signals alone, the conductive loop is closed to stimulate the electrically excitable tissue for therapeutic effect even when a significant level of external signal is present. When an external signal is applied on that closed conductive loop, unwanted current may be induced in the conductive loop which can cause undesirable physiological effects.

Thus, the conductive loop is opened when an external signal is present no matter what the first and second control signals may be. The over-sense control signal applied on the second control terminal 338 allows for an override of the first and second control signals. Thus far, the over-sense control signal has been tied low such that only the first and second control signals dictate whether the switch 302 is on or off.

However, when the over-sense control signal is set high, this signal sets the output of the third NOR gate 344 high no matter what the first and second control signals may be. As discussed previously, when the output of the third NOR gate is high, the switch turns off and introduces a high impedance into the conductive loop to open the conductive loop. Thus, by setting the over-sense control signal applied on the second control terminal 338 high, the conductive loop is opened no matter what the first and second control signals may be. In this manner, the conductive loop is opened when a significant level of an external signal such as a time-alternating electromagnetic field is present even if the conductive loop were closed for therapeutic effect.

This over-sense control signal can be generated by two means. First, the user can actively set the over-sense control signal high when the user is about to enter an area where the level of external signal is likely to be greater than an external signal threshold level. For example, in the implanted medical device system 100 of FIG. 1B, the user can send a control signal via the programmer 112 to set the over-sense control signal high. In this manner, the user controls the opening of the conductive loop before the external signal having a level which is greater than the external signal threshold level causes unwanted physiological effects.

Alternatively, a high over-sense control signal is automatically generated when an external signal is sensed by using an external signal sensor. Such a sensor can include a field sensing coil, a chattering reed switch, or a hall effect sensing switch. These sensors are commonly available and act as a switch to toggle between two states when the level of a magnetic field is greater than the external signal threshold level and when the level of a magnetic field is less than the external signal threshold level.

Figure 4:
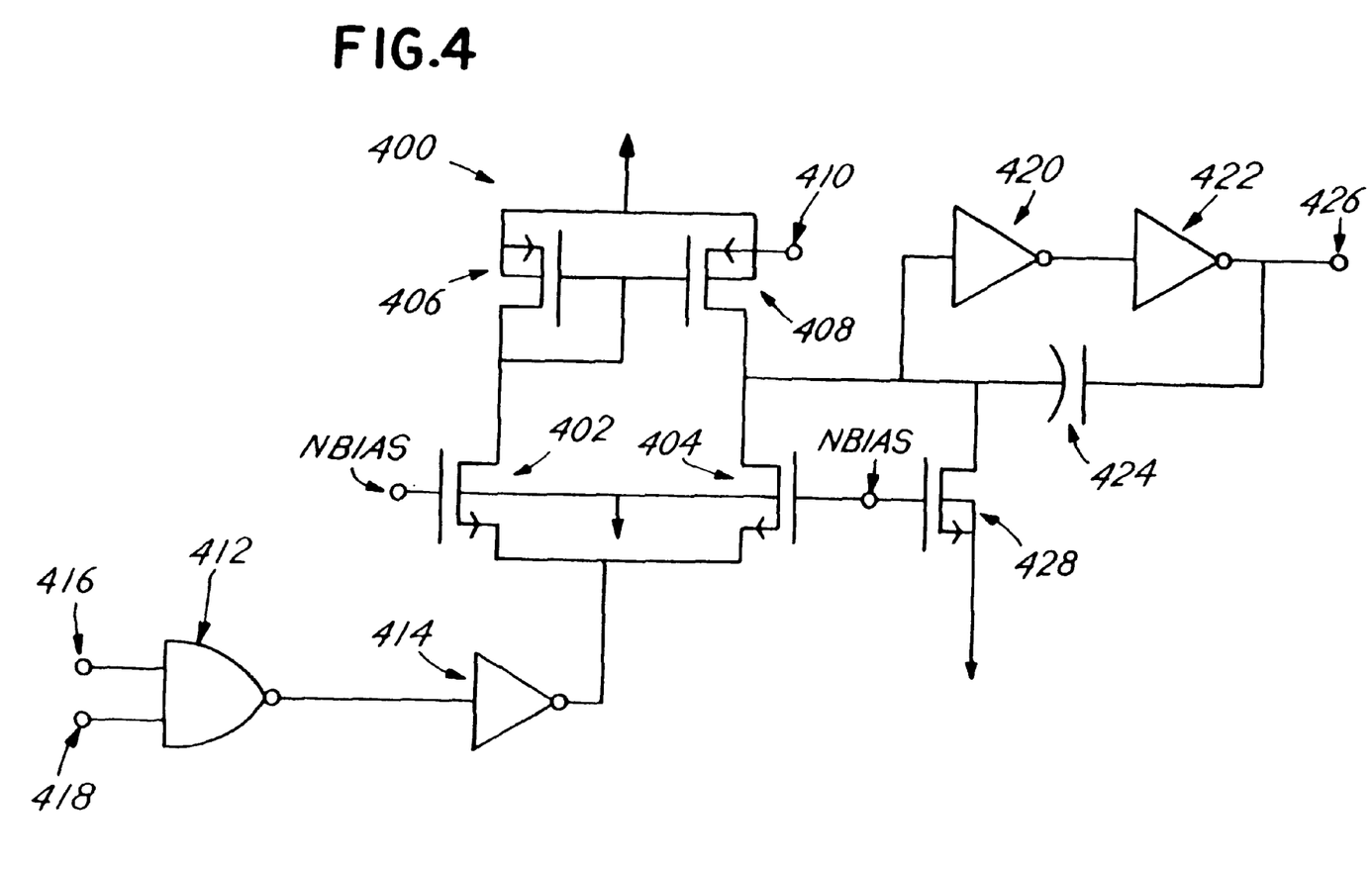
FIG. 4 shows an external signal sensor circuit according to a preferred embodiment of the present invention.

In an alternative embodiment of the present invention, the external signal sensor is implemented using CMOS technology devices. Such an external signal sensor circuit 400 is shown in FIG. 4. This circuit includes a first NMOSFET device 402 and a second NMOSFET device 404 that form matched constant current sources. The gate terminals of both of those devices are tied to a biasing circuit that can provide a NBIAS signal to appropriately bias those NMOSFET devices according to the common art of transistor circuit design. A first PMOSFET device 406 and a second PMOSFET device 408 form a current source mirror pair that also operates as a common gate differential current amplifier according to the common art of transistor circuit design. The source terminal 410 of the second PMOSFET 408 is operatively connected to the node 330 of FIG. 3.

A NAND gate 412 and a first inverter 414 effectively form an AND gate with the output of that gate being operatively connected to the common source node of NMOSFETs 402 and 404. A first NAND input terminal 416 is tied to the first control terminal 336 of FIG. 3, and a second NAND input terminal 418 is tied to the third control terminal 342 of FIG. 3.

The output of the differential amplifier pair of PMOSFETs is at the drain terminal of the second PMOSFET 410. A positive feedback loop, including a second inverter 420, a third inverter 422, and a charging capacitor 424, is operatively connected between the output of the differential amplifier and a over-sense node 426. This over-sense node is operatively connected to the second control terminal 338 of the current limiting circuit 300 of FIG. 3 and provides the over-sense control signal. A current pulling NMOSFET 428 is operatively connected at the output of the differential amplifier. The gate of that device is also tied to the biasing circuit that can provide the NBIAS signal to appropriately bias that NMOSFET.

The operation of the external signal sensor circuit 400 is now described referring to both FIGS. 3 and 4. The first NAND input terminal 416 which is tied to the first control terminal 336 of FIG. 3 receives the first control signal. The second NAND input terminal 418 which is tied to the third control terminal 342 of FIG. 3 receives the second control signal. The overall functional purpose of the external signal sensor circuit is to automatically open the conductive loop formed by an implanted medical device when the level of an external signal is greater than the external signal threshold level. Thus, the operation of this circuit is not critical when the conductive loop is already open in the case the conductive loop is not stimulating the electrically excitable tissue for therapeutic effect.

In that case, the first and second control signals are both set high, and the output of the first inverter 414 is set high. Because of a high voltage at the source terminals of the NMOSFETs 402 and 404 of the matched constant current sources, those NMOSFETs are turned off which consequently turns off the pair of PMOSFETs 406 and 408. The current pulling NMOSFET 428 is still on and discharges the output node of the differential amplifier which in turn sets the over-sense node 426 low. The over-sense signal is set low because with the first and second control signals set high, the conductive loop is already opened.

In contrast, in the case the conductive loop is already closed to stimulate the electrically excitable tissue for therapeutic effect, the output of the first inverter 414 is set low since either the first control signal or the second control signal is set low. With a low voltage at the source terminals of the NMOSFETs 402 and 404, those NMOSFETs are turned on. Consequently, the pair of PMOSFETs 406 and 408 are turned on. Thus, the matched constant current sources of the NMOSFETs 402 and 404 are appropriately biased to conduct current.

Note that the source terminal of the second PMOSFET 408 is operatively connected to the node 330 of FIG. 3. This node has a change in voltage if an external signal is present to cause a change in the current flowing in the conductive loop. Thus, the external signal sensor circuit 400 detects a significant level of unwanted current in the conductive loop that indirectly indicates the presence of a significant level of external signal.

Typically, the external signal is an AC signal, and the voltage change at the node 330 goes up and down along with the external AC signal. In the external signal sensor circuit 400 of FIG. 4, the differential amplifier senses a first positive change in the voltage at the node 330. With that positive voltage change, the current flowing through the second PMOSFET 408 increases. This increase in current charges up the output node of the differential amplifier pair to drive the over-sense node 426 high. When the level of external signal is above an external signal threshold level, the voltage on the over-sense node charges up to a high enough level which opens the conductive loop when applied on the second control terminal 338 of FIG. 3.

The positive feedback loop, which includes the second inverter 420, the third inverter 422, and the charging capacitor 424, provides positive feedback for coupling any positive change at the output of the differential amplifier to the over-sense node 426. This positive feedback loop, which may include a Schmitt trigger inverter as one of the second and third inverters, can cause an immediate voltage change on the over-sense node when the voltage goes positive. The charging capacitor 424 in this loop keeps the over-sense node positive once that node has gone positive even when the AC external signal causes a negative voltage change at the node 330 of FIG. 3.

In this manner, the external signal sensor circuit 400 of FIG. 4 can generate an over-sense control signal to be applied on the second control terminal 338 of the current limiting circuit 300 of FIG. 3. The external signal sensor circuit 400 of FIG. 4 determines when a significant level of external signal is present to automatically ensure that the conductive loop is opened. Thus, unwanted current that may be induced in the conductive loop by the external signal is automatically limited using the external signal sensor circuit.

The advantages of the invention described herein can be generalized to any partially or fully implanted medical device that forms a conductive loop with the electrically excitable tissue. In addition, the invention can be generalized to medical devices implanted in any living organism having electrically excitable tissue that can be electrically stimulated for therapeutic effect. Moreover, the invention can be generalized to any means for introducing a high impedance into that conductive loop when an external signal such as a time-alternating electromagnetic field is present.

Also, the invention can be generalized to prevent a build-up of any level of unwanted voltages in the implanted medical device. The level of unwanted voltages that can be handled by the present invention is limited by the breakdown voltage of the specific technology that is used in the implementation of the present invention. Accordingly, the forgoing description is by way of example only. The invention is limited only as defined in the following claims and equivalents thereof.

We claim:

1. A method for limiting unwanted current, induced when the level of an external signal is greater than an external signal threshold level, in a conductive loop formed by a medical device implanted within a living organism having electrically excitable tissue, the method including the steps of:

A. closing said conductive loop when said medical device is stimulating said electrically excitable tissue for achieving a therapeutic effect if the level of said external signal is less than said external signal threshold level; and B. opening said conductive loop by generating and maintaining a high impedance within said conductive loop whenever the level of said external signal is greater than said external signal threshold level, wherein said living organism manually initiates said opening of said conductive loop when said living organism is about to enter an area where the level of said external signal is greater than said external signal threshold level.

2. A method for limiting unwanted current, induced when the level of an external signal is greater than an external signal threshold level, in a conductive loop formed by a medical device implanted within a living organism having electrically excitable tissue, said method including the steps of:

A. closing said conductive loop when said medical device is stimulating said electrically excitable tissue for achieving a therapeutic effect if the level of said external signal is less than said external signal threshold level;

B. opening said conductive loop by generating and maintaining a high impedance within said conductive loop whenever the level of said external signal is greater than said external signal threshold level, wherein said living organism manually initiates said opening of said conductive loop when said living organism is about to enter an area where the level of said external signal is greater than said external signal threshold level; and C. sensing said external signal to automatically perform step B, wherein said step C includes the step of sensing the level of said unwanted current induced in said conductive loop, wherein a significant level of said unwanted current in said conductive loop indicates that the level of said external signal is greater than said external signal threshold level.

3. A current limiting apparatus that is adapted to be operatively connected as part of a conductive loop formed by a medical device implanted within a living organism having electrically excitable tissue, said current limiting apparatus comprising:

a switch, adapted to be operatively connected within said conductive loop, that turns on to close said conductive loop and that turn off to open said conductive loop; and means for controlling said switch to turn said switch on when said medical device is stimulating said electrically extitable tissue to achieve a therapeutic effect if the level of an external signal is less than an external signal threshold level, and to turn said switch off whenever the level of said external signal is greater than said external signal threshold level, wherein said switch further comprises:
a first switch device, operatively connected within said conductive loop, that turns on when said means for controlling turns said switch on and that turns off when said means for controlling turns said switch off;
a second switch device, operatively connected within said conductive loop, that turns on when said means for controlling turns said switch on and that turns off when said means for controlling turns said switch off,
wherein the first switch device and the second switch device are operatively coupled in series such that the first switch device prevents parasitic current flow through said second switch device when the external signal causes voltage build-up to a positive polarity within the conductive loop, and such that said second switch device prevents parasitic current flow through said first switch device when the external signal causes voltage build-up to a negative polarity within the conductive loop; and
a control terminal, operatively coupled to the means for controlling, that receives a control signal sent by said living organism, wherein said living organism manually initiates turning off said switch by sending said control signal to said control terminal when said living organism is about to enter an area where the level of said external signal is greater than said external signal threshold level, and wherein said means for controlling turns said switch off when said control terminal receives said control signal sent by said living organism.

4. A current limiting apparatus that is adapted to be operatively connected as part of a conductive loop formed by a medical device implanted within a living organism having electrically excitable tissue, said current limiting apparatus comprising:
a switch, adapted to be operatively connected within said conductive loop, that turns on to close said conductive loop and that turns off to open said conductive loop;
means for controlling said switch to turn said switch on when said medical device is stimulating said electrically excitable tissue to achieve a therapeutic effect if the level of an external signal is less than an external signal threshold level, and to turn said switch off when the level of said external signal is greater than said external signal threshold level,
a control terminal, operatively coupled to the means for controlling, that receives a control signal sent by said living organism, wherein said living organism manually initiates turning off said switch by sending said control signal to said control terminal when said living organism is about to enter an area where the level of said external signal is greater than said external signal threshold level, and wherein said means for controlling turns said switch off when said control terminal receives said control signal sent by said living organism; and
an external signal sensor for sensing said external signal, wherein said means for controlling turns said switch off when said sensor senses that the level of said external signal is greater than said external signal threshold level, wherein said external signal sensor senses the level of said unwanted current induced in said conductive loop, wherein a significant level of said unwanted current in said conductive loop indicates that the level of said external signal is greater than said external signal threshold level.

5. A current limiting apparatus that is adapted to be operatively connected as part of a conductive loop formed by a medical device implanted within a living organism having eletrically excitable tissue, said current limiting apparatus comprising:
means for switching said conductive loop between being closed and being open; and
a control circuit, operatively connected to said means for switching, that controls said means for switching to close said conductive loop when said medical device is stimulating said electrically excitable tissue to achieve a therapeutic effect if the level of an external signal is less than an external signal threshold level, and the controls said means for switching to open said conductive loop whenever the level of said external signal is greater than said external signal threshold level
where said means for switching further comprises:
a first switch device, operatively connected within said conductive loop, that turns on when said control circuit closes said conductive loop and than turns off when said control circuit opens said conductive loop; an
a second switch device, operatively connected within said conductive loop, that turns on when said control circuit closes said conductive loop and that turns off when said control circuit opens said conductive loop,
wherein the first switch device and the second switch device are operatively coupled in series that the first switch device prevents parasitic current flow through said second switch device when the external signal causes voltage build-up to a positive polarity within the conductive loop, and such that said second switch device prevents parasitic current flow through said first switch device when the external signal causes voltage build-up to a negative polarity within the conductive loop;
a control terminal, operatively coupled to the means for controlling, that receives a control signal sent by said living organism, wherein said living organism manually initiates opening said conductive loop by sending said control signal to said control terminal when said living organism is about to enter an area where the level of said external signal is greater than said external signal threshold level, and wherein said means for controlling turns said switch off when said control terminal receives said control signal sent by said living organism; and
means for sensing said external signal, wherein said control circuit controls said means for switching to open said conductive loop when said means for sensing senses that the level of said external signal is greater than the external signal threshold level.

6. A current limiting apparatus that is adapted to be operatively connected as part of a conductive loop formed by a medical device implanted within a living organism having electrically excitable tissue, said current limiting apparatus comprising:
means for switching said conductive loop between being closed and being open;

a control circuit, operatively connected to said means for switching, that controls said means for switching to close said conductive loop when said medical device is stimulating said electrically excitable tissue to achieve a therapeutic effect if the level of an external signal is less than an external signal threshold level, and that controls said means for switching to open said conductive loop whenever the level of said external signal is greater than said external signal threshold level, a control terminal, operatively coupled to the means for controlling, that receives a control signal sent by said living organism, wherein said living organism manually initiates opening of said conductive loop by sending said control signal to said control terminal when said living organism is about to enter an area where the level of said external signal is greater than said external signal threshold level, and wherein said means for controlling turns said switch off when said control terminal receives said control signal sent by said living organism; and means for sensing said external signal, wherein said control circuit controls said means for switching to open said conductive loop when said means for sensing senses that the level of said external signal is greater than the external signal threshold level.

7. A method for limiting unwanted current, induced when the level of a magnetic field generated by an external magnetic system is greater than a threshold level, in a conductive loop formed by a medical device implanted within a living organism having electrically excitable tissue, the method including the steps of:

A. detecting the level of said magnetic field when said living organism is substantially near the external magnetic system;

B. closing said conductive loop when said medical device is stimulating said electrically excitable tissue for achieving a therapeutic effect if the level of said magnetic field that is detected is less than said threshold level; and C. opening said conductive loop by generating and maintaining a high impedance within said conductive loop whenever the level of said magnetic field that is detected is greater than said threshold level.

8. A current limiting apparatus that is adapted to be operatively connected as part of a conductive loop formed by a medical device implanted within a living organism having electrically excitable tissue, said current limiting apparatus comprising:

a sensor for detecting the level of a magnetic field generated by an external magnetic system;

a switch, adapted to be operatively connected within said conductive loop, that turns on to close said conductive loop and that turns off to open said conductive loop; and a control circuit, operatively coupled to the sensor and the switch, for controlling said switch to turn said switch on when said medical device is stimulating said electrically excitable tissue to achieve a therapeutic effect if the level of the magnetic field that is detected by the sensor is less than a threshold level, and to turn said switch off whenever the level of the magnetic field that is detected by the sensor is greater than said threshold level.

* * * * *

UNITED STATES PATENT AND TRADEMARK OFFICE
CERTIFICATE OF CORRECTION

PATENT NO. : 6,198,972 B1
DATED : March 6, 2001
INVENTOR(S) : Hartlaub et al.

It is certified that error appears in the above-identified patent and that said Letters Patent is hereby corrected as shown below:

Column 12,
Line 65, "that turn off" should read -- that turns off --

Column 13,
Line 1, "extitable tissue" should read -- excitable tissue --

Signed and Sealed this

Fourth Day of December, 2001

*Attest:*

*Attesting Officer*

NICHOLAS P. GODICI
*Acting Director of the United States Patent and Trademark Office*